United States Patent [19]

Harasawa et al.

[11] Patent Number: 4,467,035
[45] Date of Patent: Aug. 21, 1984

[54] CULTIVATION OF PHOTOTROPHIC BACTERIA IN THE ABSENCE OF ULTRAVIOLET LIGHT

[75] Inventors: Isamu Harasawa, Kiyose; Yukio Hariki, Funabashi; Katsuhiko Maeda, Uozu; Koichi Nakamura, Uozu, all of Japan

[73] Assignee: Nippon Carbide Kogyo Kabushiki Kaisha, Tokyo, Japan

[21] Appl. No.: 403,731

[22] PCT Filed: Dec. 4, 1980

[86] PCT No.: PCT/JP80/00294
§ 371 Date: Jul. 16, 1982
§ 102(e) Date: Jul. 16, 1982

[87] PCT Pub. No.: WO82/01890
PCT Pub. Date: Jun. 10, 1982

[51] Int. Cl.[3] .......................... C12N 1/20; C12N 1/00; C12R 1/01

[52] U.S. Cl. ................................. 435/253; 210/601; 210/605; 210/620; 435/267; 435/268; 435/801; 435/818; 435/822

[58] Field of Search ............... 435/252, 253, 267, 268, 435/801, 818, 170; 210/601, 605, 620

[56] References Cited

U.S. PATENT DOCUMENTS 3,525,671 8/1970 Hitzman ..................... 435/801 X

FOREIGN PATENT DOCUMENTS 156588 12/1980 Japan .

Primary Examiner—David M. Naff
Attorney, Agent, or Firm—Wenderoth, Lind & Ponack

[57] ABSTRACT

Cultivation of phototrophic bacteria such as in the treatment of organic wastes is carried out in a light field substantially free from ultraviolet light having a wavelength of not more than 340 nm. This process promotes growth of the phototrophic bacteria and improves quality of the resulting bacterial cell.

12 Claims, 1 Drawing Figure

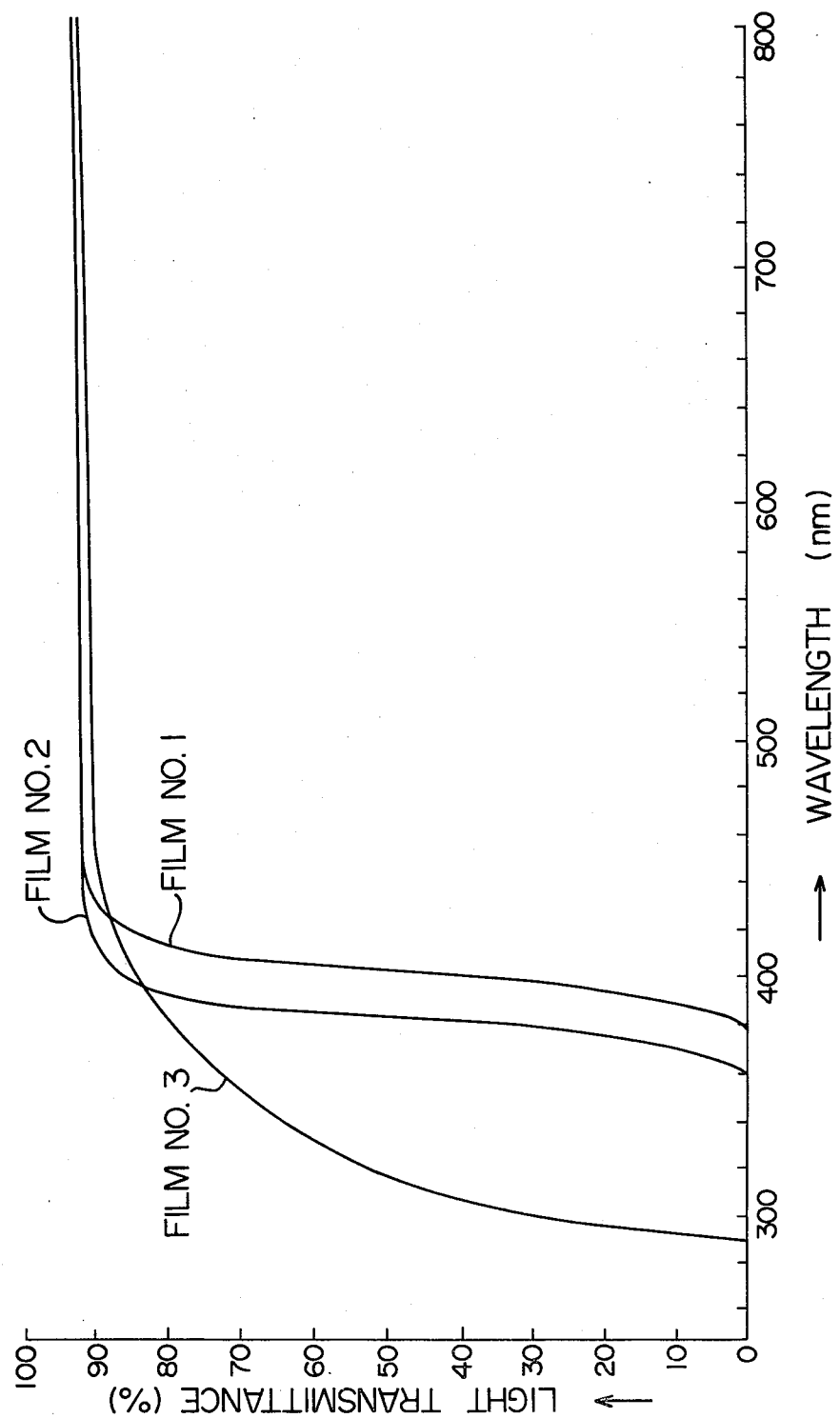

CULTIVATION OF PHOTOTROPHIC BACTERIA IN THE ABSENCE OF ULTRAVIOLET LIGHT

FIELD OF TECHNOLOGY

This invention relates to the cultivation of phototrophic bacteria, and more specifically, to an improved process for cultivating phototrophic bacteria which is intended for promotion of growth of phototrophic bacteria and increase their yield and quality.

BACKGROUND ART

In the purification treatment of organic waste waters, methods have heretofore been utilized which involve use of various microorganisms such as methane-fermenting bacteria, acid-fermenting bacteria, cellulose-decomposing bacteria and starch-decomposing bacteria. Among these methods, a method involving using phototrophic bacteria has recently aroused interest as a method which enables purification of high-concentration waste water without dilution and at the same time utilization of by-product microbial cells as resources (e.g., animal feeds, fertilizers, etc.), that is to say, a method which makes possible energy saving, resource (water) saving and utilization of discarded matter. This method is actually utilized in high-load (high-concentration) treatment of organic waste waters, for example human and domestic animal urine and feces or exrements, or effluents of the organic industry resulting from food processing, manufacture of oils and fats, sugar production, leather manufacture, etc.

This treatment method utilizing phototrophic bacteria has the defect of requiring about 7 to about 20 times as long a treating time as methods using activated sludge which are now most generally employed. Thus, in spite of its capability of high-concentration treatment of organic waste waters, its utilization in organic effluent treatment plants has not increased significantly. Some measures for shortening the treating time have been suggested heretofore (see, for example, Japanese Patent Publications Nos. 1197/67, 12631/70, 18670/71, 45881/72, 45885/72, and 43311/76).

Utilization of phototrophic bacteria in other industrial fields include a method in which a dye such as carotinoid as a microbial cell product or extract is utilized (see Japanese Patent Publication No. 9749/77 and Japanese Laid-Open Patent Publication No. 70085/77), a method of producing vitamin $B_{12}$ (see Japanese Patent Publication No. 13434/70), a method of producing nucleic acid (see Japanese Laid-Open Patent Publication No. 125697/77), a method of producing antivirally active substance (see Japanese Laid-Open Patent Publication No. 155697/75), etc. Furthermore, feeds for domestic animals and fish (see Japanese Patent Publications Nos. 1353/69, 6863/70, and 16772/72), fertilizer ingredients (see Japanese Patent Publication No. 14091/70), etc. have been proposed as uses of the microbial cells themselves. Some kinds of phototrophic bacteria generate hydrogen upon absorption of solar energy, and their use as a hydrogen supply source has also been considered.

In whichever industrial field the phototrophic bacteria are utilized, promotion of the growth of the phototrophic bacteria and increasing of the quality of the microbial cells are important in increasing the utilization of the phototrophic bacteria.

DISCLOSURE OF THE INVENTION

In order to promote the growth of phototrophic bacteria and increase the quality of the microbial cells, the present inventors have studied promotion of their growth and increasing of their yields and quality mainly with regard to the quality of light. It has now been found quite unexpectedly that when phototrophic bacteria are cultivated in a light field substantially free from ultraviolet light below a certain wavelength, the growth of the photographic bacteria can be promoted and the contents of vitamins, proteins, etc. in the resulting microbial cells can be greatly increased.

According to this invention, there is provided a process for cultivating phototrophic bacteria which comprises cultivating the phototrophic bacteria in a light field substantially free from ultraviolet light having a wavelength of 340 nm or below.

The phototrophic bacteria to which the process of this invention can be applied are a kind of aquatic microorganisms, and occur widely in nature in the anaerobic layer of water in seas, lakes, marshes, ponds, etc. They are Gram-negative bacteria which under anaerobic and visible light irradiating conditions, grow phototrophically by utilizing light energy, and which even under visible light-irradiating aerobic conditions and dark conditions, decompose inorganic and organic matters and grow by gaining energy therefrom.

Taxonomically, the phototrophic bacteria to which the process of this invention can be applied belong to the four Families, i.e. Family Rhodospirillaceae of Order Rhodospirillales and Suborder Rhodospirillineae), Family Chromatiaceae, Family Chlorobiaceae of Suborder Chlorobiineae, and Family Chloroflexaceae. The taxonomical characteristics of the phototrophic bacteria belonging to these families are tabulated in Table 1 below.

TABLE 1

| Family | Taxonomical characteristics of phototrophic bacteria | | | | | | |
|---|---|---|---|---|---|---|---|
| | Color of the culture broth | Bacteriochlorophyll | Phototrophic organ | Hydrogen donor in photosynthesis reaction | Accumulation of sulfur particles | Main carbon sources | Motility |
| Rhodospirillaceae | Red, pink, violet, orange, light brown | a or b | Chromatophore | Organic matter | | Organic matter | + |
| Chromatiaceae | Red, pink, violet, brown | a or b | Chromatophore | $H_2S$ | Intracellular | $CO_2$ | ± |
| Chlorobiaceae | Green | a and c d or e | Chlorobium vegecle | $H_2S$ | Extracellular | $CO_2$ | — |
| Chloroflexaceae | Green, orange | a and c | Chlorobium vegecle | Organic matter, | Extracellular | Organic matter, | + |

TABLE 1-continued

Taxonomical characteristics of phototrophic bacteria

| Family | Color of the culture broth | Bacterio-chloro-phyll | Phototrophic organ | Hydrogen donor in photosynthesis reaction | Accumulation of sulfur particles | Main carbon sources | Motility |
|---|---|---|---|---|---|---|---|
| | | | | $H_2S$ | | $CO_2$ | |

Typical examples of phototrophic bacteria having the above taxonomical characteristics are shown below. Most of the bacterial strains exemplified below are deposited as freely distributable strains in American Type Culture Collection (ATCC) at 12301 Parklawn Drive, Rockville, Md. 20852, U.S.A.) or Institute for Fermentation Osaka (IFO) at 2-17-85, Jyuso-honmachi, Yodogawa-ku, Osaka, Japan. Thus, where available, the deposit numbers of these strains described in the ATCC or IFO catalogs are also attached.

[I] Family Rhodospirillaceae
(I-1) Genus Rhodopseudomonas
    Rps. acidophila (ATCC 25092),
    Rps. capsulata (ATCC 11166, 17016–17022 and 23782),
    Rps. gelatinosa (ATCC 17011, 17013 and 17014),
    Rps. palustris (ATCC 17001–17010, and 25852),
    Rps. spheroides (ATCC 17023–17029, 21286 and 21455, and IFO 12203),
    Rps. viridis (ATCC 19567).
(I-2) Genus Rhodospirillum
    Rs. molishianum (ATCC 1401),
    Rs. photometricum (ATCC 27871),
    Rs. rubrum (ATCC 277, 9791, 11170, 17031–17034, 17036, 19613, 25903 and 27048; IFO 3986).
(I-3) Genus Rhodomicrobium
    Rm. vanniellii (ATCC 17100)
[II] Family chromatiaceae
(II-1) Genus Chromatium
    Chr. vinosum (ATCC 17899),
    Chr. buderi (ATCC 25583 and 25588),
    Chr. warmingii (ATCC 14959).
(II-2) Genus Thiospirillum
    Ts. winogradsky
(II-3) Genus Thiocapsa
    Tc. floridana
[III] Family Chlorobiaceae
(III-1) Genus Chlorobium
    Chl. thiosulfatophilum (ATCC 17092).
[IV] Family Chloroflexaceae
(IV-1) Genus Chloroflexus
    Chl. aurantiacus (ATCC 29362–29364, and 29366).

Among these phototrophic bacteria, those belonging to Families Rhodospirillaceae and Chloroflexaceae are preferred. In the Family Rhodospirillaceae, those belonging to the genera Rhodopseudomonas and Rhdospirium are preferred, and in the Family Chloroflexaceae, those belonging to the genus Chloroflexus are especially preferred.

The above phototrophic bacteria are used in various applications depending upon their characteristics. Examples of phototrophic bacteria used in treating excrements and organic waste waters discharged in the processing of foods and the production of oils and fats and fermented products are those of the genera Rhodospirillum, Rhodopseudomonas, Rhodomicrobium, and Chromatium. Examples of phototrophic bacteria which generate hydrogen are those of the genera Chromatium, Rhodopseudoomonas, Chlorobium, Thiospirillum and Rhodospirillum.

For treatment of organic waste waters, Rhodopseudomonas spheroides, Rhodopseudomonas capsulata, Rhodopseudomonas gelatinosa, Rhodopseudomonas palustris, Rhodospirillum rubrum and Rhodospirillum photometricum, above all Rps. spheroides and Rs. rubrum, are now frequently used. The process of this invention can also be preferably applied to these bacterial strains.

In accordance with the process of this invention, the aforesaid phototrophic bacteria are cultivated in a light field substantially free from ultraviolet light having a wavelength of not more than 340 nm, preferably not more than 360 nm and more preferably not more than 380 nm.

The term "light field substantially free from light having a wavelength of not more than X nm" denotes not only a light field in which ultraviolet light having a wavelength of not more than X nm is completely absent, but also a light field which contains the ultraviolet light of the aforesaid wavelength region in such a small amount which does not adversely affect the cultivation in accordance with this invention. Furthermore, the term "light field" denotes a field which at least contain light having a wavelength in a visible region (about 400 nm to 800 nm) (white light, monochromatic light, or complex colored light), and may optionally contain ultraviolet light and/or infrared light.

When the process of this invention is carried out under irradiation of sunlight, it is desirable to cultivate phototrophic bacteria in a light field in which at least 70%, preferably at least 80%, more preferably 90 to 100%, of the ultraviolet light in the above-mentioned wavelength region is inhibited. On the other hand, when the cultivation is carried out using artificial light rays, it is desirable to cultivate phototrophic bacteria under irradiation of light in which the amount of the ultraviolet light in the aforesaid wavelength region is not more than 1000 $\mu\omega/cm^2$, preferably not more than 500 $\mu\omega/cm^2$, more preferably 200 to 0 $\mu\omega/cm^2$, using a light filter as required.

The phototrphic bacteria can grow both under dark conditions and visible light-irradiating conditions. In the process of this invention, however, light at least within the visible region is positively irradiated to promote growth of phototrophic bacteria, as stated hereinabove. Accordingly, in performing the process of this invention, some irradiation of light in the visible region, namely the light field, is required. Desirably, the process of this invention is carried out in a light field which contain light having a wavelength of generally at least 450 nm, preferably at least 420 nm. The intensity of light in a wavelength region of at least 450 nm varies greatly according to the type of the phototrophic bacterium to be cultivated, the depth of the culture medium, etc. and cannot be definitely determined. However, by performing small-scale experiment, the amount and intensity of light can be easily determined by any one skilled in the art.

Light having a wavelength of 340 nm to 450 nm, namely, the near ultraviolet to violet light, may or may not be present in the light field. Minimization of the amount of such light shows a favorable tendency to the growth of phototrophic bacteria.

Except for the use of the above-specified light field, the cultivation of phototrophic bacteria in accordance with this invention can be performed by conventional cultivation methods without requiring any special conditions.

Methods that can be employed for providing the specified light field include a method which involves irradiating artificial light rays free from light of wavelengths of not more than 340 nm, preferably not more than 360 nm, and more preferably not more than 380 nm, and desirably containing light of wavelengths of at least 420 nm (in this case, a source of the artificial light rays may emit light having such optical properties, or the light irradiated from such an artificial light source through a suitable filter); a method involving irradiating sunlight through a transparent colorless or colored covering material which substantially inhibits transmission of light of wavelengths of not more than 340 nm, preferably not more than 360 nm, more preferably not more than 380 nm; and a combination of these two methods.

When an organic effluent is to be treated by using, for example, phototrophic bacteria belonging to the genus Rhodopseudomonas or Rhodospirillum, the aforesaid light field is formed on the water surface of a pool or pond by covering the entire surface with a specified covering material to be described, and these phototrophic bacteria are cultivated in the pool or pond. As is usual, an organic waste water subjected to solubilization treatment which contains various wastes, for example organic acids such as acetic acid, butyric acid, succinic acid and malic acid, organic materials such as mannitol, glucose, fructose and starch, and tiny amounts of iron, magnesium, etc. is introduced into the pool or pond, and aerated with stirring, and a phototrophic microorganism is inoculated. Preferably, the temperature of water is maintained generally at about 10° C. to about 40° C. (generally 25° to 35° C.) and the luminance of the light, at 1000 to 6000 lux. Under these conditions, the cultivation can be performed for 1 to 3 days. As a result, the water in the pool or pond is purified. The solid residue may be separated in a customary manner, for example by filtration.

The organic effluent or water which can be treated by the process of this invention may, for example, be human and domestic animal excrements; sewage; and organic effluents from oils and fats plants or food manufacturing and processing plants for sugar, flour, starch, marine products, fruit juices and fermented products. In treating these organic effluents with phototrophic bacteria in accordance with the process of this invention, the organic effluents are generally subjected to solubilization treatment beforehand. The solubilization treatment denotes a procedure whereby water-insoluble high molecular organic substances are decomposed under aerobic conditions into lower fatty acids, amino acids and other low-molecular organic substances by various heterotrophic microorganisms or enzymes. Of course, the solubilization treatment is not required for organic waste waters which do not contain high-molecular organic substances. A specific procedure for the solubilization treatment comprises adding a heterotrophic microorganism such as Bacillus, Staphylococcus, Proteus, Clostridium and Bacterium and if required an enzyme for decomposition of cellulose, starch, etc. to an organic effluent containing high molecular organic substances, and treating the mixture under aerobic conditions at about 30° C. for 1 to 3 days. At this stage, the organic high molecular substances are decomposed to lower fatty acids (e.g., acetic acid, propionic acid and butyric acid), amino acids and other lower molecular organic acids by the action of the heterotrophic microorganism or the enzyme, and these low molecular substances constitute nutrient sources for phototrophic bacteria. In the solubilizing tank, anaerobic bacteria in the waste water and microorganisms seen in general activated sludges are decreased in number to some extent owing to aeration and the presence of high-concentration organic acids.

The organic effluent so subjected to solubilization treatment is then transferred to a sterilization tank where various contaminating bacteria in the effluent are killed as much as possible by treatment with chlorine, sodium chlorate, gamma-rays, ultraviolet rays, ultrasonic waves, etc. Furthermore, when the biochemical oxygen demand (BOD) of the effluent is too high, the effluent is diluted to adjust its BOD to about 5,000 to about 50,000 ppm, and the pH is adjusted to 6.5 to 7.5.

Then, in the organic effluent so solubilized, a phototrophic bacteria strain is inoculated in accordance with the process of this invention. The number of the phototrophic bacterial strains inoculated at this time may generally be about $10^7$ to $10^{10}$ cells/ml although it varies depending upon the type of the strains, etc. The solubilized organic effluent may be an effluent of high concentration containing having a biochemical oxygen demand (BOD) of at least 1,000 ppm, preferably about 5,000 to about 50,000 ppm.

The cultivation can be performed under aerobic or anaerobic conditions. Generally, the use of aerobic conditions seems to give a greater effect of promoting bacterial growth. Desirably, the cultivation is carried out at a pH of about 6 to about 9.

The organic effluent solubilized as above, for example body excrement, is treated with a phototrophic bacterial strain in the specified light field in accordance with the process of this invention. Specific examples of the treating process are shown below.

An effective cultivation tank for phototrophic bacteria is a multi-tank system comprising a plurality of tanks connected to each other according to the degree of pollution of the waste effluent. An example of the cultivation tank is a tank fitted with a closure made of a transparent polyvinyl chloride plate with substantially inhibits transmission of ultraviolet light having a wavelength of not more than 360 nm, preferably not more than 380 nm and permits substantial transmission of light having a wavelength of at least 420 nm. Two to six such cultivation tanks are installed in a place where sufficient sunlight falls, and $10^7$ to $10^{10}$ of cells of the bacterial strain are inoculated and cultivated at 25° to 35° C. while bubbling sterilized air and stirring the cultivation system in order to maintain aerobic conditions. The cultivation is carried out for 1 to 3 days while successively transferring the effluent at a speed corresponding to a residence time of about 1 to ½ day per tank. The biochemical oxygen demand of the effluent is initially 5,000 to 50,000, but is decreased to 200 to 500 ppm as a result of the cultivation. The purified effluent is discharged.

The process of this invention can also be applied to a pure culture of phototrophic bacteria. The composition of a culture medium used at this time may be varied depending upon the type of the bacterial strain to be cultivated, etc. Generally, culture media for phototrophic bacteria can be prepared by mixing organic compounds, for example lower fatty acids such as acetic acid, propionic acid and butyric acid, alcohols such as ethanol, glycerol, mannitol and sorbitol, organic acids such as malic acid, succinic acid, citric acid, crotonic acid and lactic acid, sugars such as glucose, fructose, mannose and maltose, organic amino acids such as glutamic acid, alanine and aspartic acid, bouillon, and various vitamins, and nitrogen, phosphoric acid, potassium, sulfur and inorganic salts such as magnesium, iron or calcium salts. [ATCC CATALOG of STRAINS of I, 13th Edition (1978), page 438; Journal of Cell Composition and Physiology, 43, pages 25–68 (1957)]. Suitable cultivation temperatures are 25° to 35° C., and the suitable pH of the culture medium is about 6.5 to about 7.5.

A suitable procedure of performing the process of this invention is to cultivate photogrophic bacteria under a transparent covering material which can form the above-specified light field, that is, which substantially inhibits transmission of ultraviolet light having a wavelength of not more than 340 nm, preferably not more than 360 nm, especially preferably not more than 380 nm, and desirably permits substantial transmission of light having a wavelength of at least 450 nm, preferably at least 420 nm.

The term "substantial inhibition of the transmission of light of the above-specified wavelength", as used herein, means not only complete inhibition of the transmission of the light of the above wavelength, but also allowing of transmission of up to 20%, preferably up to 10%, more preferably up to 5%, of the ultraviolet light of the above-specified wavelength.

The term "substantial transmission" of the light of having a wavelength of at least Y nm means not only complete transmission of light having a wavelength of at least Y nm, but also transmission of up to 60%, preferably up to 75%, more preferably up to 90%, of the light having the above-specified wavelength without any deleterious effect.

The covering material may substantially permit transmission of the light having a wavelength region of 340 nm to 450 nm, or may substantially inhibit its transmission. Conveniently, the average transmittance of the light having the above wavelength region is adjusted generally to 10 to 95%, preferably 30 to 90%.

The material for the covering material of this invention is not particularly restricted so long as it has the aforesaid light-transmitting properties. Usually, the covering material of this invention may be composed of an inorganic or organic film, plate and other shaped article. Typical examples of the inorganic film or plate include a glass plate containing a dye or pigment (Emerald Green), and a glass plate having a plastic film containing an ultraviolet absorber of the types exemplified hereinbelow coated or laminated thereon. Plastic films or plates having an ultraviolet absorber coated thereon or incorporated therein are especially preferred.

Box-like, hollow or foamed articles of synthetic resins containing ultraviolet absorbers can also be used as the covering material of this invention floating on the water surface. In addition to thermoplastic resins to be described hereinbelow, thermosetting resins such as melamine resin, phenol resin, epoxy resin, silicone resin, urea resin, alkyd resin, and allyl phthalate resin can also be used.

Plastic films or plates containing ultraviolet absorbers are especially suitable as the covering material of this invention. These plastic films and plates are described in detail hereinbelow. (In the present invention, the term "plate" is used to embrace tubular and box-like structures as well.)

Transparent films or plates that can be used in this invention can be produced, for example by blending an ordinary film-forming thermoplastic resin with a suitable ultraviolet absorber, and shaping the mixture into a film or sheet.

Examples of the film-forming thermoplastic synthetic resins are polyvinyl chloride, polyvinylidene chloride, polyethylene, polypropylene, polystyrene, polyesters, polyamides, polycarbonate, polymethyl methacrylate, acrylate resins, polyvinyl acetate, polyvinyl alcohol, fluorine-containing resins, cellulosic resins, ABS resin, copolymers consisting mainly (preferably at least 50% by weight) of the monomeric units of these polymers, and blends of these polymers or copolymers. From the viewpoint of light resistance, strength and light transmitting property, polyvinyl chloride, polyethylene, polypropylene, fluorine-containing resins, cellulosic resins and polystyrene are preferred.

Ultraviolet absorbers having the ability to substantially inhibit the transmission of light of wavelengths of not more than 340 nm when incorporated into the aforesaid synthetic resins can be selected from a wide range of species according to their ultraviolet absorbing ability, their compatibility with the synthetic resins, etc. Examples of such ultraviolet absorbers are listed below.

Hydroquinone compounds

Hydroquinone and hydroquinone disalicylate.

Salicylic acid compounds

Phenyl salicylate and p-octylphenyl salicylate.

Benzophenone compounds

2-Hydroxy-4-methoxybenzophenone,
2-hydroxy-4-n-octoxybenzophenone,
2-hydroxy-4-methoxy-2-carboxybenzophenone,
2,4-dihydroxybenzophenone,
2,2'-dihydroxy-4,4'-dimethoxybenzophenone,
2-hydroxy-4-benzyloxybenzophenone,
2,2'-hydroxy-4-methoxybenzophenone,
2-hydroxy-4-methoxy-5-sulfonebenzophenone,
2,2',4,4'-tetrahydroxybenzophenone,
2,2'-hydroxy-4,4'-dimethoxy-5-sodiumsulfobenzophenone,
4-dodecyloxy-2-hydroxybenzophenone, and
2-hydroxy-chlorobenzophenone.

Benzotriazole compounds 2-(2'-hydroxy-5'-methylphenyl)benzotriazole,
2-(2'-hydroxy-5'-methylphenyl)-5-butylcarbonate benzotriazole,
2-(2'-hydroxy-5'-methylphenyl)-5,6-dichlorobenzotriazole,
2-(2'-hydroxy-5'-methylphenyl)-5-ethylsulfonebenzotriazole,
2-(2'-hydroxy-5'-tert-butylphenyl)-5-chlorobenzotriazole,
2-(2'-hydroxy-5'-tert-butylphenyl)benzotriazole, 2-(2'-hydroxy-5'-aminophenyl)benzotriazole,
2-(2'-hydroxy-3',5'-dimethylphenyl)benzotriazole,
2-(2'-hydroxy-3',5'-dimethylphenyl)-5-methoxybenzotriazole,
2-(2'-methyl-4'-hydroxyphenyl)benzotriazole,
2-(2'-stearyloxy-3',5'-dimethylphenyl)-5-methylbenzotriazole,
2-(2'-hydroxy-5'-phenylcarbonate)benzotriazole ethyl ester,
2-(2'-hydroxy-3'-methyl-5'-tert-butylphenyl)benzotriazole,
2-(2'-hydroxy-3',5'-di-tert-butylphenyl)-5-chloro-benzotriazole,
2-(2'-hydroxy-5'-methoxyphenyl)benzotriazole,
2-(2'-hydroxy-5'-phenylphenyl)-5-chlorobenzotriazole,
2-(2'-hydroxy-5'-dichlorohexylphenyl)benzotriazole,
2-(2'-hydroxy-4',5'-dimethylphenyl)-5-carboxylic acid benzotriazole butyl ester,
2-(2'-hydroxy-3',5'-dichlorophenyl)benzotriazole,
2-(2'-hydroxy-4',5'-dichloro)benzotriazole,
2-(2'-hydroxy-3',5'-dimethylphenyl)-5-ethylsulfonebenzotriazole,
2-(2'-hydroxy-5'-phenylphenyl)benzotriazole,
2-(2'-hydroxy-4'-octoxyphenyl)benzotriazole,
2-(2'-hydroxy-5'-methoxyphenyl)-5-methylbenzotriazole,
2-(2'-hydroxy-5'-methylphenyl)-5-carboxylic acid ester benzotriazole,
2-(2'-acetoxy-5'-methylphenyl)benzotriazole,
2-(2'-hydroxy-3',5'-di-tert-butylphenyl)-5-chlorobenzotriazole,
2-(2'-hydroxy-3'-tert-butyl-5'-methylphenyl)-5-chlorobenzotriazole,
2-(2'-hydroxy-3'-tert-butyl-5'-methylphenyl)-5,6-dichlorobenzotriazole, and
2-(2'-hydroxy-3',5'-di-tert-butylphenyl)-4,4-dichlorobenzotriazole.

Among these ultraviolet absorbers, the benzophenone compounds and the benzotriazole compounds are preferred. Among the benozophenone compounds, 2,3'-dihydroxy-4,4'-dimethoxybenzophenone, 2,2'-dihydroxy-4-methoxybenzophenone and 2,2',4,4'-tetrahydroxybenzophenone are especially preferred. On the other hand, especially preferred benzotriazole compounds are 2-(2'-hydroxy-5'-methylphenyl)benzotriazole, 2-(2'-hydroxy-5'-methylphenyl)-5,6-dichlorobenzotriazole, 2-(2'-hydroxy-5'-tert-butylphenyl)benzotriazole, 2-(2'-hydroxy-3'-methyl-5'-tert-butylphenyl)benzotriazole, 2-(2'-hydroxy-3',5'-di-tert-butylphenyl)-5-chloro-benzotriazole, 2-(2'-hydroxy-5'-phenylphenyl)-5-chlorobenzotriazole, 2-(2'-hydroxy-3',5'-di-tert-butylphenyl)-5-chlorobenzotriazole, 2-(2'-hydroxy-5'-octoxyphenyl)benzotriazole, 2-(2'-hydroxy-3'-tert-butyl-5'-methylphenyl)-5-chlorobenzotriazole, and 2-(2'-hydroxy-3'-tert-butyl-5'-methylphenyl)-5,6-dichlorobenzotriazole.

Especially preferred ultraviolet absorbers are benzotriazole derivatives of the following formula

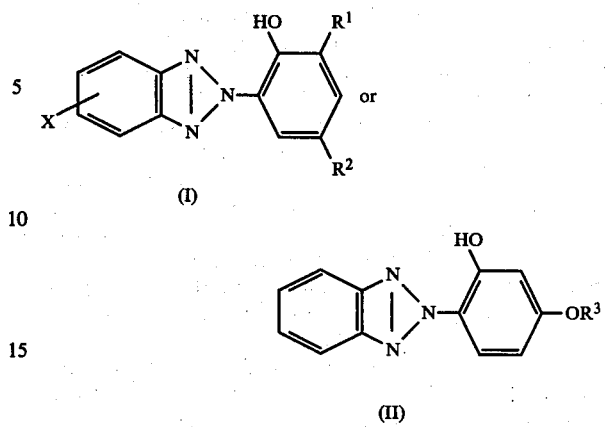

wherein $R^1$ and $R^2$ are identical or different and each represents a lower alkyl group or an aryl group, especially a phenyl group, $R^1$ preferably representing a branched lower alkyl group having not more than 5 carbon atoms or a phenyl group, $R^3$ represents as alkyl group containing at least 6 carbon atoms, especially 8 to 10 carbon atoms, and X represents a hydrogen atom or a halogen atom, especially a chlorine atom.

The amount of the ultraviolet absorber can be varied over a wide range depending upon the type of the ultraviolet absorber, the type of the synthetic resin used, the thickness of the film or plate, etc. It has been found that in order to achieve substantial inhibition of the transmission of ultraviolet rays having a wavelength of not more than 340 nm, preferably not more than 360 nm, especially preferably not more than 380 nm, the following relation is preferably established between the amount of the ultraviolet absorber and the thickness of the resulting film or plate.

$$15 \leq AB \leq 600,$$

preferably $$20 \leq AB \leq 400$$

in which A is the amount (PHR) of the ultraviolet absorber, and B is the thickness (microns) of the film or plate. PHR denotes the number of parts by weight per 100 parts by weight of the synthetic resin.

The suitable amount (A) of the ultraviolet absorber is generally 0.001 to 5 PHR, and in the case of a film, preferably 0.1 to 5.0 PHR.

In addition to the ultraviolet absorber, the synthetic resin used in this invention may contain small amounts of other conventional additives such as plasticizers, lubricants, antioxidants, light stabilizers, antistatic agents, moisture-proofing agents, heat stabilizers, dyes, pigments, and agents for preventing adhesion of unwanted algae, shellfish, and other fouling materials.

The plastic film, plate or other shaped articles can be produced by various known methods, for example a calendering method, a melt-extrusion method such as inflation, a press method, a solution casting method, or an injection molding method. To prevent the physical properties of the film from deterioration, another resin may be coated on it, or another film may be laminated on it.

The thickness of the film, plate and other shaped article can be varied widely. Generally, to active the objects of this invention, the suitable thickness is 15 to 5,000 microns, especially 20 to 3,000 microns. As required, the film or plate may be laminated on another plastic film or sheet or a glass sheet in order to reinforce it. The plastic film or sheet, especially the former, may also be reinforced with reinforcing fibers such as glass fibers, wire meshes, or a net-like fibrous structure.

As required, to prevent adhesion of shellfish, algae and fouling materials to the covering material of this invention which results in reduced transparency, the covering material of this invention may be surface-treated with a chemical for inhibiting the adhesion of shellfish and algae, or a synthetic resin containing such a chemical may be coated or laminated on it.

In forming the specified light field using the covering material of this invention, it is not necessary to shield the entire cultivation system of phototrophic bacteria from ultraviolet rays of the specified wavelength region. Usually, it is sufficient to cover the cultivation system such that it substantially inhibits transmission of the light of the aforesaid wavelength region which may be present in irradiating light (e.g., direct sunlight).

Usually, direct sunlight and indirect scattered light exist as the light to be irradiated on phototrophic bacteria in their cultivation under sunlight. In the process of this invention, it is at least necessary to protect the phototrophic bacteria from the direct sunlight.

Various methods of covering the cultivation system with the covering material of this invention according to the cultivation environment, the stage of growth, etc. are available. For example, a frame is built up over the water surface of a cultivating area for phototrophic bacteria (e.g., pool, pond, lake, sea), and the covering material is stretched over the frame. Or the covering material is stretched on the water surface in a floating manner. Or supporting posts are provided under the water, and the covering material is stretched over these posts. Or the cultivation liquor is passed through a tubular covering material (i.e., pipe). Also, the cultivation may be carried out in a box-like covering material. Combinations of these methods can also be employed.

The following examples further illustrate the present invention. All percentages in these examples are by weight unless otherwise specified.

The films used in the following examples and comparative examples were prepared as described below.

(1) One hundred parts by weight of polyvinyl chloride, 45 parts by weight of dioctyl phthalate (plasticizer), 1.5 parts by weight of dibutyltin maleate (heat stabilizer), 1.0 part by weight of zinc stearate (heat stabilizer), 0.1 part by weight of stearic acid (lubricant), 1.0 part of sorbitan monolaurate (anticloud agent), and 1.5 parts by weight of 2-(2'-hydroxy-3',5'-di-tert-butylphenyl)-chlorobenzotriazole (ultraviolet absorber) were fully mixed with each other. The mixture was melt-extruded through an extruder at 200° C. to obtain a transparent film having a thickness of 0.1 mm. This film is designated as film No. 1, and used as a covering material in the following examples.

(2) A film having a thickness of 0.1 mm was prepared in the same way as in (1) above except that the ultraviolet absorber was changed to 1.4 parts by weight of 2-(2'-hydroxy-5'-methylphenyl)-benzotriazole. The The resulting film was designated as film No. 2.

(3) For comparison, a polyvinyl chloride film (thickness 0.1 mm; "NOBI ACE" made by Mitsubishi Monsanto Chemical Co., Ltd.), marketed as a general agricultural covering material, was provided. This film is designated as "film No. 3".

BRIEF DESCRIPTION OF THE DRAWING

The light transmission curves at different wavelengths of the films Nos. 1 to 3 are shown in FIG. 1 of the accompanying drawing.

EXAMPLES 1 AND 2 AND COMPARATIVE EXAMPLE 1

Into each of 300 ml Roux-type flasks made of hard glass permitting transmission of light having a wavelength of at least 300 nm was poured 100 ml of a culture medium consisting of 0.05% of potassium monohydrogen phosphate ($K_2HPO_4$), 0.05% of potassium dihydrogen phosphate ($KH_2PO_4$), 0.08% of ammonium monohydrogen phosphate [$(NH_4)_2HPO_4$, 0.02% of magnesium sulfate ($MgSO_4.7H_2O$), 0.01% of sodium chloride (NaCl), 0.04% of calcium chloride ($CaCl_2.2H_2O$), 1.0 mg/liter of niacin, 1.0 mg/liter of thiamine HCl, 0.04 mg/liter of biotin, and 0.3% of sodium acetate ($CH_3COONa$), and the medium was sterilized at 120° C. for 15 minutes. Then, *Rhodopseudomonas spheroides* (IFO 12203) ($1.4 \times 10^7$ cells/ml) was aseptically inoculated. Each flask was stopped with a cotton stopper, and set in a shaking cultivation machine in a darkroom.

A combination of a pure color fluorescent lamp FL-40S-W-EDL-50K (a product of Tokyo Shibaura Electric Co., Ltd.) and a black light fluorescent lamp FL-40S-BLB (a product of Tokyo Shibaura Electric Co., Ltd.) was set as a light source in a light projector in the darkroom. The light from the light source was adjusted so that the intensity of the near ultraviolet region (300 to 400 nm) was 2000 $\mu\omega/cm^2$ (measured by an ultraviolet intensity meter UVR-365, a product of Tokyo Optical Instrument Co., Ltd.; the same method is used hereinbelow) and the illuminance of the visible light region (400 to 800 nm) was 6,000 lux (measured by Spectrophotometer and Radiometer Model 301, a product of Photo Research Co., U.S.A.). The fluorescent lamps in the light source section were completely covered with the film No. 1, 2 or 2 prepared above, and the cultivation was carried out at a temperature of 27±1° C. for 60 minutes with 120 shaking cycles. The number of microbial cells grown as a result of the cultivation was counted by using a Thoma's counting chamber (the same method is used in the following examples).

The results are shown in Table 2.

TABLE 2

| Run | Covering film No. | Number of bacterial cells ($\times 10^7$/ml) 40 hours later | 60 hours later |
|---|---|---|---|
| Example 1 | 1 | 27 | 110 |
| Example 2 | 2 | 15 | 54 |
| Comparative Example 1 | 3 | 8.5 | 21 |

EXAMPLES 3 AND 4 AND COMPARATIVE EXAMPLE 2

(A) Example 1 was repeated except that the culture medium was changed to the culture medium of Cohen-Bazier, W. R. Sistrom and R. Y. Stanier [Journal of Cell Composition and Physiology, 43, 25–68 (1957)], and the cultivation temperature was changed to 30° C. (aerobic cultivation).

(B) In the procedure of (A) above, a gaseous mixture composed of 95% by volume of nitrogen gas and 5% by volume of carbon dioxide gas was bubbled at a rate of 600 ml/min. during the cultivation (anaerobic cultivation).

In both (A) and (B), the cultivation was carried out for 20 hours, and the number of bacterial cells grown was countered. The results are shown in Table 3.

TABLE 3

| Run | Covering film No. | Number of bacterial cells ($\times 10^7$/ml) | |
| --- | --- | --- | --- |
| | | Aerobic cultivation | Anaerobic cultivation |
| Example 3 | 1 | 88 | 440 |
| Example 4 | 2 | 53 | 350 |
| Comparative Example 2 | 3 | 24 | 140 |

EXAMPLES 5 AND 6 AND COMPARATIVE EXAMPLE 3

The same cultivation as in Example 1 was performed for 48 hours under aerobic conditions except that the sterilizing step was omitted, the culture medium was changed to solubilized human excrement (BOD 8,500 ppm) adjusted to pH 6.8 with sulfuric acid, and the cultivating temperature was changed to 30° C. The results are shown in Table 4.

The used human excrement was obtained at Iriyoshi-cho, Toyama Prefecture, Japan after solubilization treatment.

TABLE 4

| Run | Covering film No. | BOD (ppm) | |
| --- | --- | --- | --- |
| | | Before testing | After 48 hours |
| Example 5 | 1 | 8,500 | 350 |
| Example 6 | 2 | 8,500 | 660 |
| Comparative Example 3 | 3 | 8,500 | 2,300 |

The BOD was measured in accordance with the method described at pages 33 to 36 of JIS K 0102-1971. (The same method was used hereinafter).

EXAMPLE 7 AND COMPARATIVE EXAMPLE 4

The same cultivation as in Example 1 was carried out for 60 hours except that the bacterial strain used was changed to *Rhodpseudomonas capsulata* (ATCC 11166), the cultivation temperature was maintained at 30±1° C., and the same anaerobic conditions as in Example 3, (B) were used.

TABLE 5

| Run | Covering film No. | Number of bacterial cells ($\times 10^7$/ml) |
| --- | --- | --- |
| Example 7 | 1 | 56 |
| Comparative Example 4 | 3 | 11 |

EXAMPLE 8 AND COMPARATIVE EXAMPLE 5

Example 1 was repeated except that in Example 1, the bacterial strain was changed to *Rhodopseudomonas gelatinosa* (ATCC 17011), and the cultivation temperature was changed to 30° C. The results are shown in Table 6.

TABLE 6

| Run | Covering film No. | Number of microbial cells ($\times 10^7$/ml) |
| --- | --- | --- |
| Example 8 | 1 | 160 |
| Comparative Example 5 | 3 | 18 |

EXAMPLES 9 AND 10 AND COMPARATIVE EXAMPLE 6

The same cultivation as in Example 3, (A) and (B) was carried out except that the bacterial strain was changed to *Rhodospirillum rubrum* (IFO 3986). The results are shown in Table 7.

TABLE 7

| Run | Covering film No. | Number of bacterial cells ($\times 10^7$/ml) | |
| --- | --- | --- | --- |
| | | Anaerobic cultivation | Aerobic cultivation |
| Example 9 | 1 | 115 | 530 |
| Example 10 | 2 | 91 | 350 |
| Comparative Example 6 | 3 | 37 | 105 |

EXAMPLE 11 AND COMPARATIVE EXAMPLE 7

Solubilized human excrement was treated in the same way as in Example 5 except that the bacterial strain was changed to *Rhodospirillum rubrum* (IFO 3986). The results are shown in Table 8.

TABLE 8

| Run | Covering film No. | BOD (ppm) | |
| --- | --- | --- | --- |
| | | Before testing | After 48 hours |
| Example 11 | 1 | 8,500 | 480 |
| Comparative Example 7 | 3 | 8,500 | 2,900 |

EXAMPLE 12 AND COMPARATIVE EXAMPLE 8

The same cultivation as in Example 3, (A) was carried out under aerobic conditions except that the bacterial strain was changed to *Rhodospirillum photometricum* (ATCC 27871) and the cultivation temperature was changed to 26° C. The results are shown in Table 9.

TABLE 9

| Run | Covering film No. | Number of bacterial cells ($\times 10^7$/ml) |
| --- | --- | --- |
| Example 12 | 1 | 630 |
| Comparative Example 8 | 3 | 120 |

EXAMPLES 13 AND 14 AND COMPARATIVE EXAMPLES 9 AND 10

Example 1 was repeated except that the bacterial strain was changed to *Rhodomicrobium vanniellii* (ATCC 17100) or *Chloroflexus aurantiacus* (ATCC 29366), the cultivation temperature was changed as shown in Table 10, and the same anaerobic conditions as in Example (B) were used. The results are shown in Table 10.

TABLE 10

| Bacterial strains | Run | Covering film No. | Cultivation temperature (°C.) | Number of bacterial strains ($\times 10^7$/ml) |
|---|---|---|---|---|
| Rm. vannicllii | Example 13 | 1 | 26 | 68 |
| | Comparative Example 9 | 3 | 26 | 25 |
| Cf. aurantiacus | Example 14 | 1 | 40 | 56 |
| | Comparative Example 10 | 3 | 40 | 22 |

What we claim is:

1. A process for producing phototrophic bacteria which comprises cultivating a phototrophic bacterium selected from the group consisting of the genera Rhodopseudomonas, Rhodospirillum, Rhodomicrobium and Chloroflexus, in a light field substantially free from ultraviolet light having a wavelength of not more than 340 nm.

2. The process of claim 1 wherein the phototrophic bacterium is cultivated in a light field substantially free from ultraviolet light having a wavelength of not more than 360 nm.

3. The process of claim 1 wherein the phototrophic bacterium is cultivated in a light field substantially free from ultraviolet light having a wavelength of not more than 380 nm.

4. The process of any one of claims 1 to 3 wherein the photographic bacterium is cultivated in a light field which may contain light of a visible region having a wavelength of at least 450 nm.

5. The process of claim 1 wherein the phototrophic bacterium is cultivated under irradiation of sunlight while covering the cultivation system with a covering material capable of substantially inhibiting transmission of ultraviolet light having a wavelength of not more than 360 nm but substantially permitting transmission of light having a wavelength of at least 450 nm to provide light substantially free from said ultraviolet light.

6. The process of claim 1 wherein the phototrophic bacterium is cultivated under irradiation of sunlight while covering the cultivation system with a covering material capable of substantially inhibiting transmission of ultraviolet light having a wavelength of not more than 360 nm and substantially permitting transmission of light having a wavelength of at least 420 nm to provide light substantially free from said ultraviolet light.

7. The process of claim 1 wherein the cultivation is carried out under aerobic or anaerobic conditions.

8. The process of claim 1 wherein the cultivation is carried out under aerobic conditions.

9. The process of claim 1 wherein the phototrophic bacterium is *Rhodopseudomonas spheroides* or *Rhodospirillum rubrum*.

10. The process of claim 1 wherein the cultivation is carried out in an organic waste water subjected to solubilization treatment and having a biochemical oxygen demand of at least 1,000 ppm at a pH of about 6 to about 9.

11. The process of claim 10 wherein the organic waste water contains human or animal excrement.

12. A process for treating human or animal excrement, which comprises stretching a covering material capable of substantially inhibiting ultraviolet light having a wavelength of not more than 360 nm and substantially permitting transmission of light having a wavelength of at least 420 nm over the surface of a tank or a pond on which sunlight can be irradiated, supplying human or animal excrement subjected to solubilization treatment and having a biochemical oxygen demand of at least 1000 ppm to the tank or pond, inoculating a phototrophic bacterium selected from the group consisting of the genera Rhodopseudomonas, Rhodospirillum, Rhodomicrobium and Chloroflexus therein, and cultivating the phototrophic bacterium until the biochemical oxygen demand of the treated solution reaches the desired value.

* * * * *